United States Patent [19]

Scott et al.

[11] Patent Number: 4,606,230

[45] Date of Patent: Aug. 19, 1986

[54] TENSILE TEST APPARATUS EMBODYING NOVEL SPECIMEN BAR MAGAZINE

[75] Inventors: Richard L. Scott; William A. Kirksey; James K. Rieke, all of Midland, Mich.

[73] Assignee: The Dow Chemical Company, Midland, Mich.

[21] Appl. No.: 752,752

[22] Filed: Jul. 8, 1985

[51] Int. Cl.[4] ............................................. G01N 3/02
[52] U.S. Cl. ........................................ 73/856; 73/826
[58] Field of Search ................ 73/856, 826, 809, 819, 73/834; 221/9, 135, 166, 175, 210, 290; 414/128, 131, 754

[56] References Cited

U.S. PATENT DOCUMENTS 3,927,558 12/1975 Philippe et al. ................. 73/834 X

FOREIGN PATENT DOCUMENTS 2084331 4/1982 United Kingdom ................. 73/826

Primary Examiner—Jerry W. Myracle

[57] ABSTRACT

A tensile testing apparatus comprises a magazine or holder for test specimens. The specimens are disposed horizontally with their end portions constrained by U-shaped channels. Slots at the lower ends of the channels are provided for pulling the lowermost test specimen therethrough under the action of robot fingers, the fingers pulling the specimen to a 90 degree slide whereupon the fingers are lowered and the test specimen slides down the slide and is rotated 90 degrees before coming to rest on seats at the ends of the slides. The now retracted robot fingers are turned 90 degrees and spread apart for movement toward the test specimen which is then gripped and lifted upwardly from the seats and then transferred to a testing machine, tested and then removed from the testing machine.

7 Claims, 10 Drawing Figures

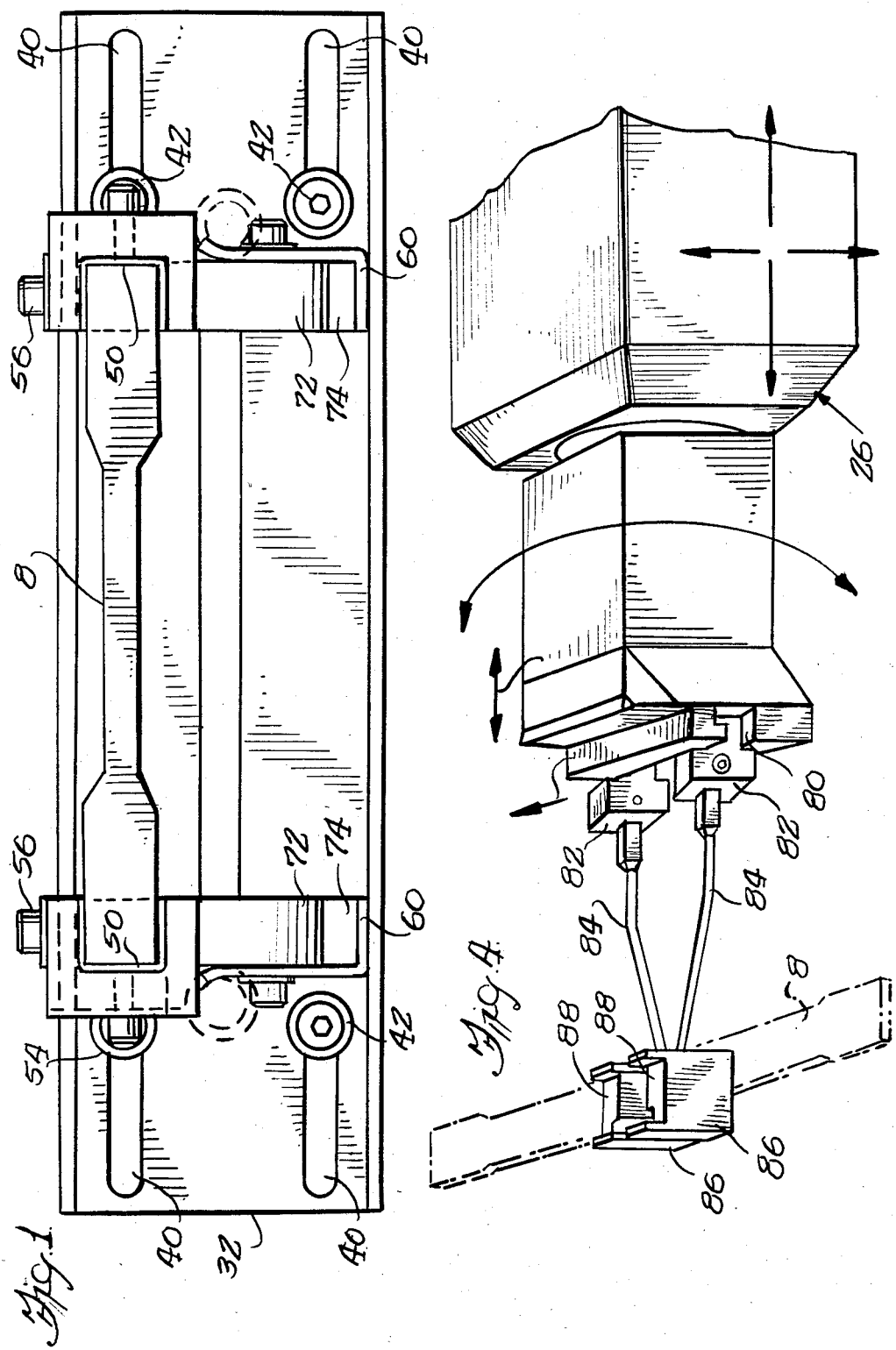

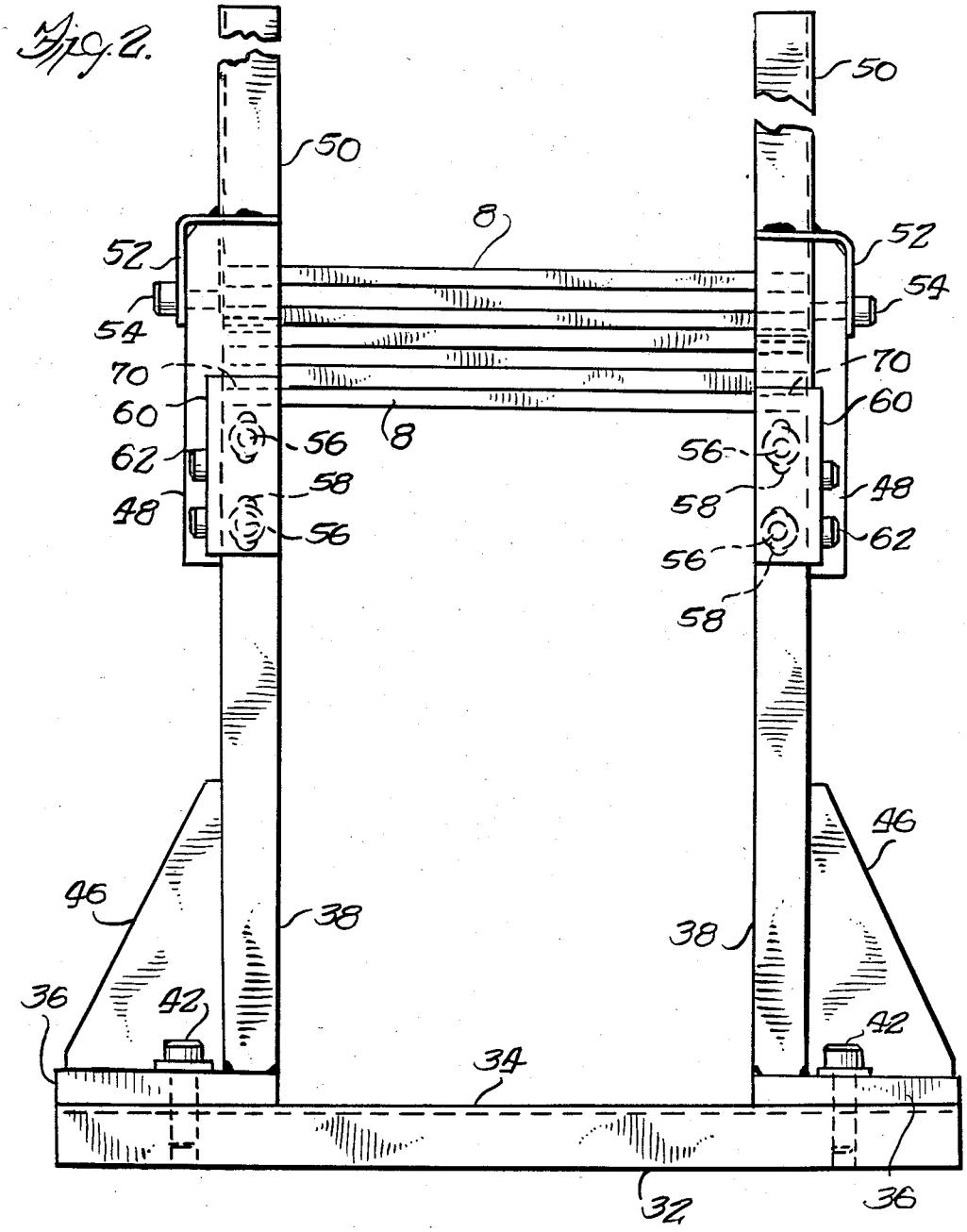

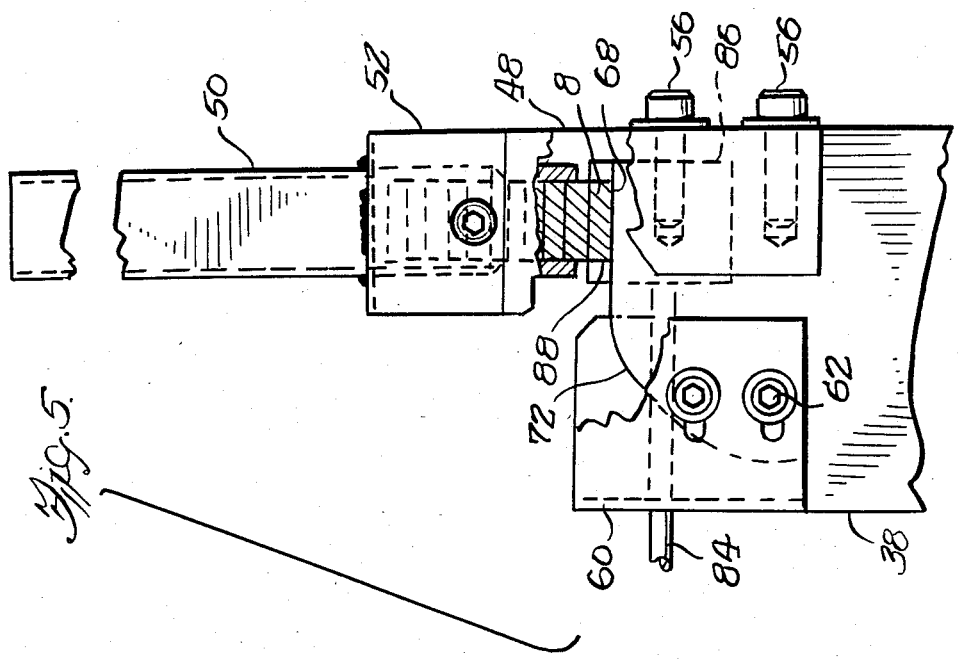
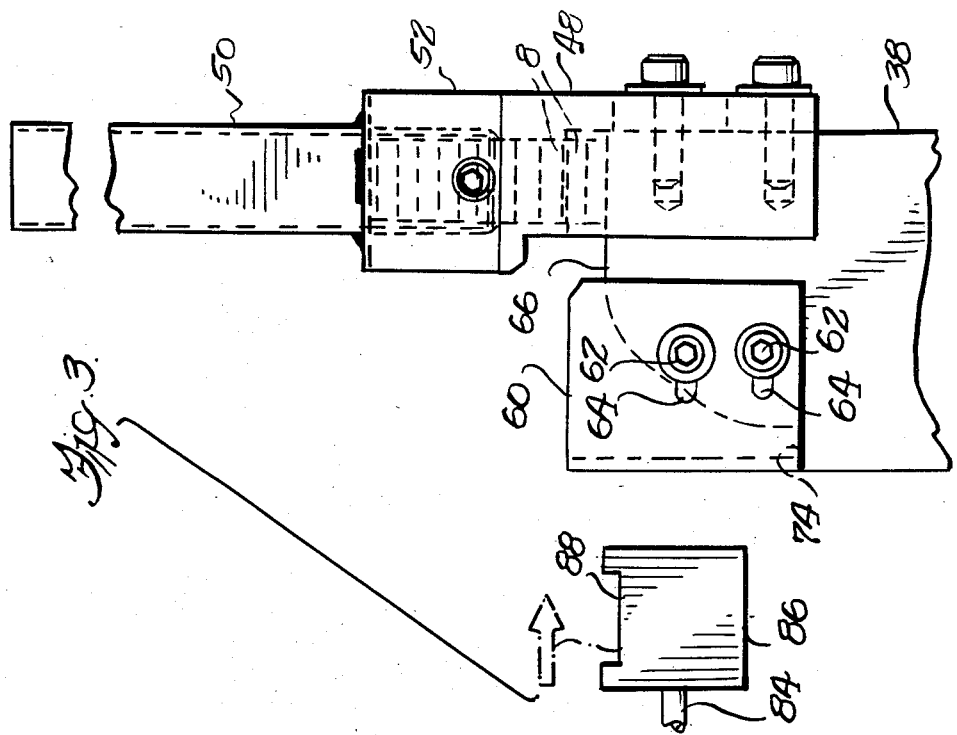

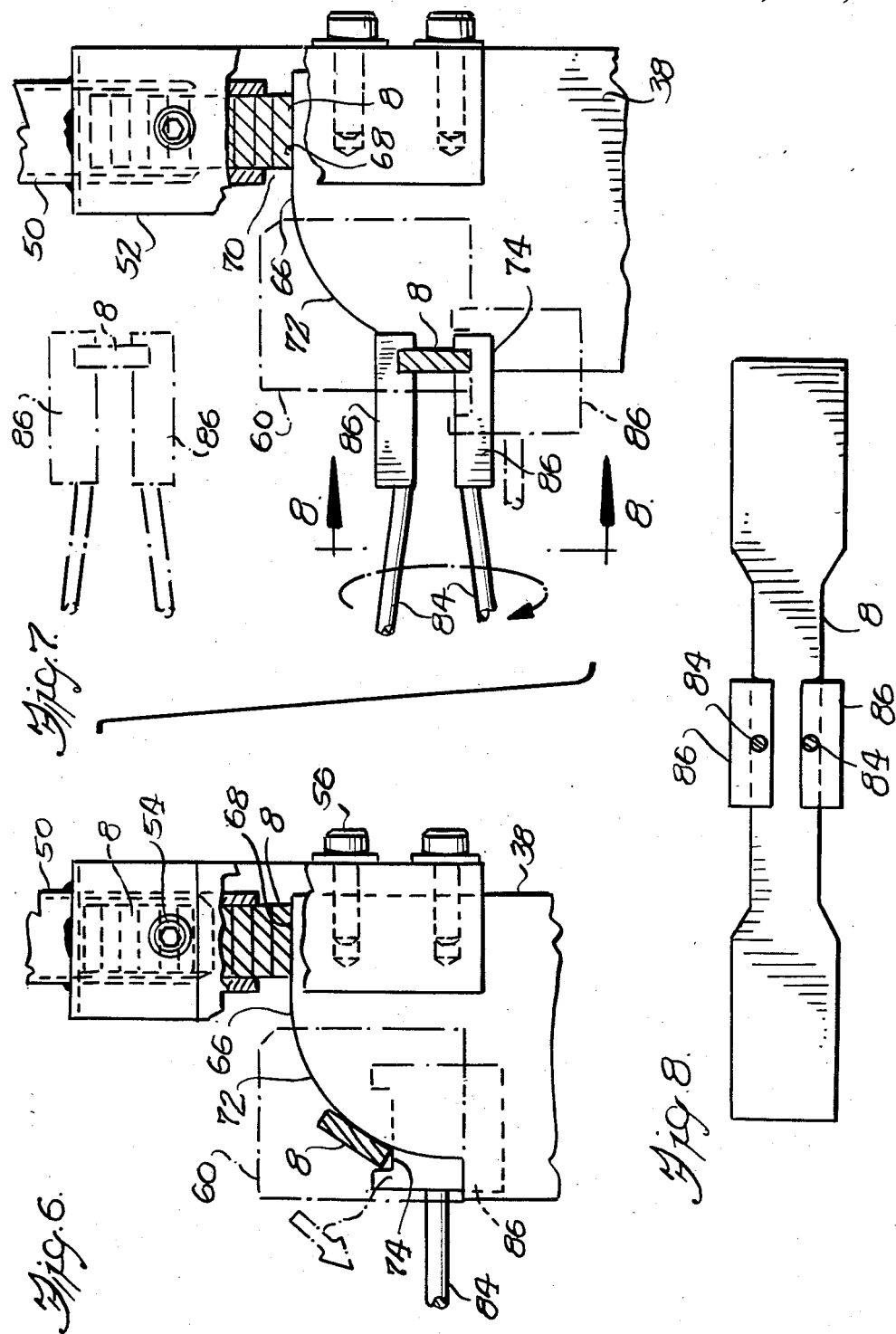

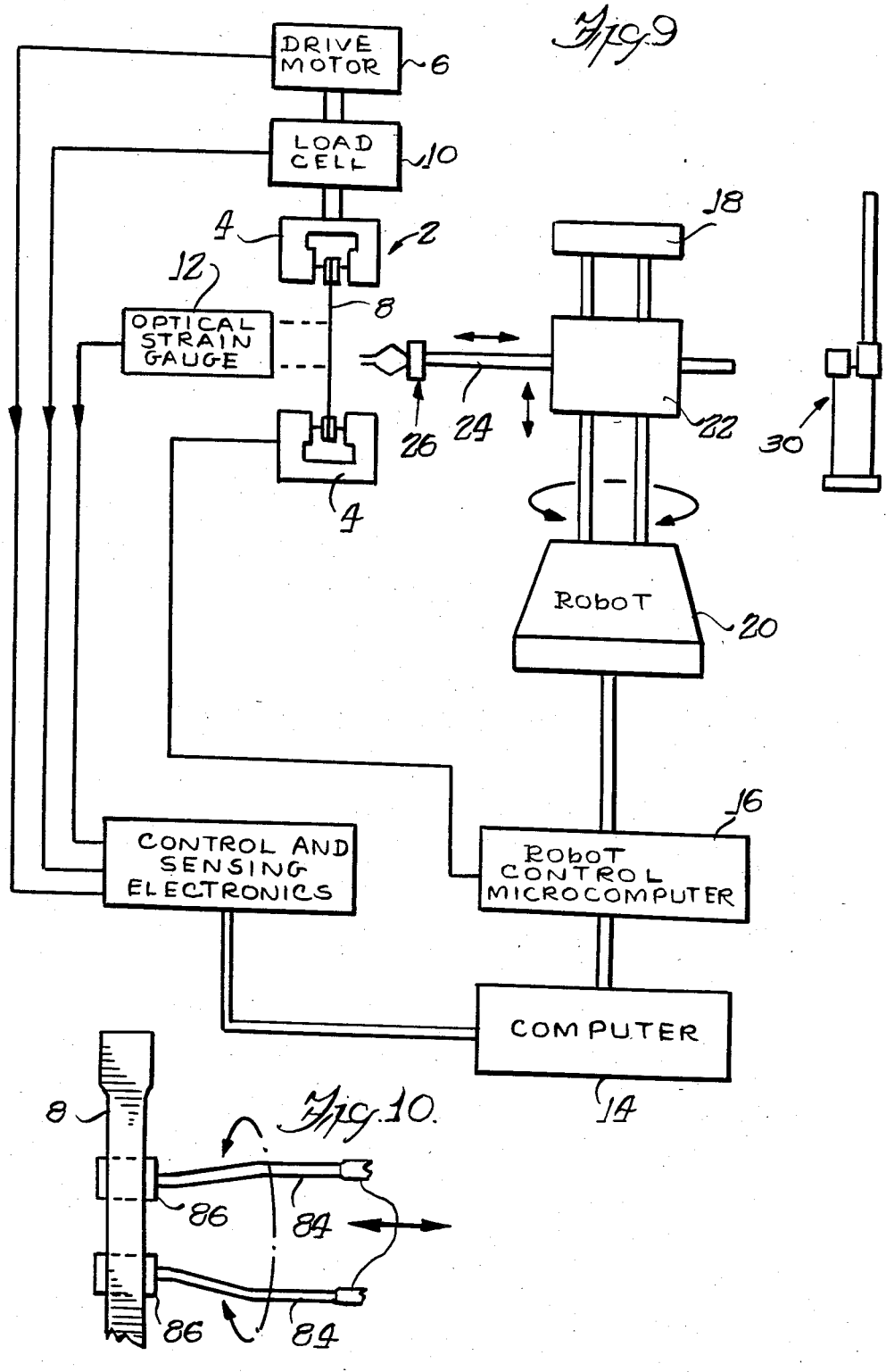

TENSILE TEST APPARATUS EMBODYING NOVEL SPECIMEN BAR MAGAZINE

BACKGROUND OF THE INVENTION

This invention relates generally to testing, and more particularly to an automatic or "robot" operated tensile test specimen apparatus that embodies a novel specimen bar holder or magazine.

In the polymer industry it is known to utilize uniaxial tensile tests to define and characterize the physical properties of both research and quality control samples of the polymer and like plastic materials. Basically, the test determines the stress on the test specimen as a function of strain under a defined set of experimental conditions. From the data such characteristics as tensile strength, ultimate strength, and modulus of elasticity may be ascertained.

In performing the aforesaid tensile test, a dumbbell-shaped test specimen is secured at its opposite ends in a testing machine. One end of the specimen is attached to a fixed grip and the other end is attached to a cross head which may be driven at a constant velocity. At one of the two grips for the test specimen there is a load cell to measure the amount of force on the specimen when it is in tension. The data may be accumulated in the form of force as a function of elongation, the increase in length as compared to original length, and other data. From such information it is possible to compute a number of physical properties, for example tensile strength at yield, yield strain, modulus of elasticity, and the like.

Tensile testing apparatus has been known for years, and generally these instruments require that the test bars be inserted and removed by hand. The relatively short duration of the tensile test makes it necessary for the operator to remain at the instrument in order to keep it in continuous operation. This of course increases the cost of performing the tests and ties up an operator who might be doing other work.

OBJECTS AND SUMMARY OF THE INVENTION

In the automated apparatus of the present invention an operator is required to load a series of test bars into the novel magazine, after which the test series is completed without further intervention of the operator. The novel test specimen magazine is designed to cooperate with the testing apparatus whereby the test bars are removed from the magazine one by one under the action of an automatic article transfer device or "robot".

Accordingly, an object of this invention is to provide a test bar magazine which may be loaded with a number of test bars in stacked relationship and withdrawn one by one automatically as is needed.

A further object of this invention is to provide an apparatus of the type stated that includes a novel magazine which is inexpensive to manufacture and is easily embodied into conventional testing hardware. A more specific object of this invention is to provide a test specimen bar magazine of the foregoing type which embodies an arrangement for placing the test bars in stacked relationship and such that the lowermost test bar may be withdrawn from a predetermined location and shifted to another location at which it may be grasped easily by an automatic transfer mechanism which picks up the bar and delivers it to a testing machine for insertion therein.

Broadly speaking, the tensile test specimen bars are stacked in the magazine or specimen bar holder in the order in which they are to be tested. The specimens are disposed horizontally with their end portions constrained by U-shaped channels so that the specimens can move only vertically. Small horizontal slots at the bottoms of the channels allow an automatic transfer arm or robotic device arm to slide the bottom specimen bar out of the constraining channels and to pull the bar forward so that it is completely outside of the slots and rests on opposed slide surfaces. The opposed slide surfaces are of a 90 degree configuration and the test bars slide downward, rotating 90 degrees in the process and becoming seated on opposed seats. Consequently, the test bar has been shifted to a position of convenience while at the same time it has been rotated 90 degrees to facilitate its being grasped by the arms of the article transfer or "robot" device. Furthermore, the robotic arm goes through a series of pre-programmed motions, as determined by a microcomputer, so as to grasp the specimen bar and lift it vertically, clearing the specimen bar holder, following which the specimen bar is delivered to the testing machine.

Viewed another way the invention comprises, in the testing apparatus, a magazine for holding a plurality of elongated test specimens, said magazine comprising opposed upstanding members spaced apart and having channels for receiving the opposite end portions of the test specimens so that a group of the test specimens is horizontally disposed but is in vertically stacked relationship and spans the space between the channels. There is provided a structure from which the upstanding members are mounted, the structures and the upstanding members defining slots at the lower ends of each channel to provide an escape passage for the test specimens exiting said channels at their lower ends, a shoulder ajacent to each said slot and upon which the lowermost test specimen rests preparatory to removal of the lowermost test specimen from the magazine, seats on each upstanding member for receiving the exiting test specimen, said seats being clear of the associated slot and shoulder, said slots being sized for one-by-one removal therethrough of said test specimen; and an article transfer device having fingers for engaging each of said specimens when the specimen becomes the lowermost specimen of the stack and serving to withdraw said specimens from the stack through the slots. There is further provided slide means on said magazine permitting the specimens that are withdrawn through the slots to slide one-by-one onto the seats, and means for moving the fingers of the transfer device to a position engaging the test specimen on the seat.

The invention may be viewed further as a magazine for a group of tensile test bars of the type and kind forming a part of the combination referred to in the previous paragraph.

BRIEF DESCRIPTION OF THE FIGURES

FIG. 1 is a top plan view of a novel magazine for test specimens constructed in accordance with and embodying the present invention;

FIG. 2 is a front elevational view thereof;

FIG. 3 is a side elevational view thereof;

FIG. 4 is a fragmentary perspective view of the head end of the robotic arm that is utilized in the present invention;

FIG. 5 is a fragmentary side elevational view, partially broken away, of a portion of FIG. 3 and showing the end portion of the robotic transfer arm preparatory to moving the lower most test specimen from the seat upon which it is disposed to a position wherein it can slide downward through a 90 degree slide and become seated in position for removal by the robotic arm;

FIG. 6 is a view similar to FIG. 5 but showing the test specimen after it has slid down the 90 degree slide and before seated in position preparatory to being removed from transfer to the testing machine;

FIG. 7 is a view similar to FIG. 6 but showing only a portion thereof and with the fingers at the end of the robotic arm being shown engaged with the test specimen for removal from the magazine;

FIG. 8 is a fragmentary sectional view taken along line 8—8 of FIG. 7;

FIG. 9 is a diagrammatic showing of the testing apparatus in which the magazine or specimen bar holder forms a part; and FIG. 10 is an enlarged structural view, partially in section, of a portion of the fingers and transfer arm of the robot or transfer device.

DETAILED DESCRIPTION OF THE ILLUSTRATED EMBODIMENT

Reference should now be made to FIG. 9 of the drawing which shows the overall configuration of the automated tensile test system. There is shown a tester 2 which is a universal testing device performing the tensile tests and is a known commercially available piece of equipment. The tester 2 is equipped with pneumatic-hydraulic grips 4 which grasp the test specimen that is undergoing the tensile test. A drive motor 6 serves as a source of power to apply the tensile force to the specimen 8, and a load cell 10 provides an analog signal corresponding to the tension applied to the specimen. An optical strain gauge 12 measures the elongation of the specimens 8 directly. Output signals from the load cell 10 and the optical strain gauge 12 are connected to suitable electronics to allow these signals to be read by the digital computer 14. Suitable electronics are also provided to allow the digital computer 14 to control the movement of the crosshead on the tester and to allow the robot control microcomputer 16 to open and close the pneumatic-hydraulic grips 4.

Handling of the test specimens is performed by a transfer device or robot generally designated at 18. The robot 18 includes a rotating base 20, a vertical crosshead 22, and a transfer arm 24. The structures 20, 22 serve to operate the transfer arm so that the hand 26 of the transfer arm 24 may have the universal movement shown by the arrows in FIGS. 4 and 9 so that the fingers and hand hereinafter described can be moved as a unit along cylindrical coordinates (FIG. 9) or the fingers and hand can be rotated as a unit. The microcomputer 16 is programmed to operate the servomotors in the robot base 20, crosshead 22, arm 24, and hand 26 in such a manner as to insert and remove test bars 8 upon receipt of appropriate commands from the computer 14. Sensing microswitches on the pneumatic-hydraulic grips are read by the microcomputer and are used to detect malfunctions in the specimen handling apparatus. The construction and arrangement of the computer 14, the microcomputer 16, and the components 20, 22, 24 are conventional except for the fingers attached to the hand 26, which fingers are hereinafter described.

Thus, the computer 14 tells the robot controlling microprocessor 16 to insert the test specimen. The microcomputer controls movements of the transfer arm 24 and also controls movements of the pneumatic-hydraulic grips 4 to insert and grip the test specimen. The computer also controls the tester's drive mechanism and records the force and strain data. Upon completion of the test the computer tells the robot controlling microcomputer 16 to remove the specimen bar from the pneumatic-hydraulic grips 4.

A specimen bar holder or magazine 30 of novel design is utilized to store a group of specimen bars 8 as will now be described. Essentially, the specimen bars are loaded into the magazine 30 that comprises a base 32 of generally rectilinear configuration and provided with a longitudinal slide 34. Within the slide 34 are the bottom flanges 36, 36 of a pair of supports or uprights 38, 38. The flanges 36, 36 are formed with elongated holes 40, 40 through which pass bolts 42, 42, whereby the spacing between the uprights 38, 38 may be adjusted and the uprights secured in place. Each upright includes a triangular gusset plate 46 for reinforcement purposes. The spacing between the uprights 38, 38 is made adjustable so that the magazine can accommodate specimens of varying lengths.

Mounted on the upper ends of the uprights 38, 38 are channel mounts 48, 48 of box-like or rectilinear shape and have welded thereto opposed channels 50, 50. Channels 50, 50 are of generally U-shaped cross section, opening toward each other and being spaced apart in an amount sufficient to receive the enlarged end portions of the test specimens 8 which span the space between the channels 50. It will be noted that the test specimens are of rectangular cross section, being longer in one dimension that the other, and being stacked with the thinner dimension of the specimens being vertical and the thicker dimension being horizontal. A channel cap 52 into which the channel 50 is directly welded is secured by a bolt 54. Furthermore, a pair of bolts 56 pass through slots 58 in the channel mounts 48 and are threaded into the uprights 38 whereby the channels 50 may be vertically adjusted relative to the uprights 38.

Mounted on the upper end portions of the uprights 38 are constraining channels 60, 60 of generally L-shape, the constraining channels 60 being secured by bolts 62, 62 which pass through elongated slots 64, 64. The bolts 62, 62 are, in turn, threaded into the upper end portions of the uprights 38.

The upper end surfaces of the uprights 38, 38 are formed with surfaces 66 having a generally horizontal portion or shoulder 68 directly under the lower ends of the channels 50. The lowermost test specimen of the stack sits on the shoulders 68 preparatory to withdrawal of the specimen from the magazine. The channels 50 are constructed and vertically positioned such that slots 70, 70 are provided and through which the lower test specimen of the stack is withdrawn. The height of each slot 70 is slightly larger than the thickness of the test bars 8, and the height of slot 70 may be adjusted by loosening bolts 56 and varying the height of the channel and channel mount structure 48, 50. At the end of the surface portion 66 remote from the slot 70 the surface portion 66 constitutes a slide 72 that runs approximately 90 degrees and terminates in a seat 74. Thus, if a specimen is withdrawn through the slot 70 and moved to the 90 degree slide 72 the test specimen will slide down the slide 72 and become seated on the seat 74, being confined thereat by flanges of the confining channel 60. This in effect causes the test specimen to rotate 90 degrees from its position on the shoulder 68.

The hand 26 of the transfer arm 24 is capable of rotational movement about its longitudinal axis, and the arm is capable of movement vertically, horizontally and rotational about a vertical axis. This gives complete freedom of movement of the hand 26 rotationally and in the X, Y, and Z directions. As seen in FIG. 4, the extreme forward end of the hand 26 is formed with a slide 80 in which finger mounts 82 are shiftable toward or away from each other. These finger mounts have rods 84, 84, the free ends of which are provided with fingers 86, 86. These fingers 86, 86 are specially formed with cutouts 88, 88 which are sized slightly larger than the width of the central portion of the test specimen so that the fingers can receive the test specimen as will now be described.

The programmed movement of the hand 26 moves the fingers 86 to a position underneath at the lowermost test specimen of the stack. The transfer arm 24 is raised so that the fingers 86 move upwardly until the test specimen 8 is positioned in the cutouts 88, 88 as best seen in FIG. 5. The fingers are then moved to the left as seen in FIG. 5 so as to pull the lowermost test specimen 8 along the surface 66 from the shoulder 68 and through the slot 70 until the test specimen reaches the arcuate slide 72. At that time the fingers 86, 86 are lowered, allowing the test specimen to rotate 90 degrees and slide along the slide 72 until the test specimen is deposited on the seat 74. This action is shown in FIG. 6 wherein the test specimen 8 is on the arcuate slide portion 72 and in FIG. 7 wherein the test specimen is shown resting upon the seats 74. The now retracted hand 26 is rotated 90 degrees about a horizontal axis to bring the opposed flat sides of the fingers 86 into the horizontal position as distinguished from the vertical positions shown in FIG. 4.

The fingers 86, 86, which are now withdrawn from the magazine, may then be spread apart following which the hand 26 may be advanced toward the magazine. The fingers 86 then come together to engage the top and bottom surfaces of the specimen as shown in full lines in FIG. 7 and in FIG. 8. Thereafter, the transfer arm 24 is elevated to lift the specimen off of the seats 74, it being necessary to raise the arm above the constraining channels 60. Thereafter, the arm 24 is rotated and otherwise moved to transfer the specimen to the tensile tester shown in FIG. 9. Consequently, the handling of the test specimens as they are withdrawn one-by-one from the supply thereof in the channels 50, 50 is completely automatic and requires only manual loading of the channels 50, 50.

The invention is claimed as follows:

1. In a testing apparatus, a magazine for holding a plurality of elongated test specimens, said magazine comprising opposed upstanding members spaced apart and having channels for receiving the opposite end portions of the test specimens so that a group of test specimens is horizontally disposed but is in vertically stacked relationship and spans the space between said channels, a structure on which said upstanding members are mounted, said structure and said upstanding members defining slots at the lower ends of each channel to provide an escape passage for test specimens exiting said channels at their lower ends, a shoulder adjacent to each said slot and upon which the lowermost test specimen rests preparatory to removal of said lowermost test specimen from the magazine, seats on each upstanding member for receiving the exiting test specimen, said seats being clear of the associated slot and shoulder, said slots being sized for one-by-one removal therethrough of said test specimens; and an article transfer device having fingers for engaging each of said specimens when the specimen becomes the lowermost specimen of the stack and serving to withdraw said specimen from the stack through the slots, slide means on said magazine permitting specimens that are withdrawn through said slots to move along the slide means one-by-one onto said seats, and means for moving said fingers to a position engaging said test specimen on said seat.

2. In a testing apparatus according to claim 1, said slide means including sections substantially 90 degrees in extent and arranged such that the test specimens slide freely down the 90 degree sections to said seats.

3. In a testing apparatus according to claim 1, said fingers having cutouts for receiving the test specimens in a manner to permit the fingers to be moved so as to pull a test specimen through said slots.

4. In a testing apparatus according to claim 3, in which said transfer mechanism has means for moving said fingers from a first position wherein the fingers support the test specimen substantially at its lower horizontal surface as the specimen is pulled through said slots to a second position in which the fingers engage opposed surfaces of the test specimens that are substantially at right angles to said lower horizontal surface.

5. A magazine for tensile test bar specimens comprising opposed upstanding members spaced apart and having upstanding channels for receiving the opposite end portions of elongated test specimens so that a group of the test specimens is horizontally disposed but is in vertically stacked relationship and spans the space between said channels, a structure upon which said upstanding members are mounted, said structure and said upstanding members defining slots at the lower ends of each channel to provide a passage for test specimens exiting the said channels at their lower ends, a shoulder adjacent to each said slot and upon which the lowermost test specimen rests preparatory to removal of said lowermost test specimen from the magazine, seats on each upstanding member for receiving the exiting test specimens, each seat being offset from the associated slot and shoulder and at least part of the region between each seat and its associated slot being a slide that permits the test specimens to move from the shoulders to the seats and rest on the seats in a different orientation from its orientation on the shoulder, means for moving the test specimen, said slots being horizontally aligned and being sized for one-by-one removal of test specimens therethrough.

6. A magazine according to claim 5, in which said slide is comprised of opposed arcuate surfaces which are aligned and each of substantially 90 degrees in extent.

7. A magazine according to claim 5, further including constraining members cooperating with said slides to maintain the test specimens on the slides as the test specimen travels therealong.

* * * * *